United States Patent
Hashino et al.

(10) Patent No.: US 8,388,794 B2
(45) Date of Patent: Mar. 5, 2013

(54) PROCESS FOR PRODUCING ADHESIVE PATCH

(75) Inventors: Ryo Hashino, Ibarak (JP); Masakatsu Konno, Ibaraki (JP); Jun Harima, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 156 days.

(21) Appl. No.: 12/503,375

(22) Filed: Jul. 15, 2009

(65) Prior Publication Data

US 2010/0012266 A1     Jan. 21, 2010

(30) Foreign Application Priority Data

Jul. 16, 2008  (JP) ................... 2008-184670

(51) Int. Cl.
*B29C 65/00* (2006.01)
*B32B 37/00* (2006.01)
*B32B 38/04* (2006.01)

(52) U.S. Cl. ...................... 156/270; 156/253
(58) Field of Classification Search ............ 156/270, 156/253, 257, 261, 264, 265
See application file for complete search history.

(56) References Cited

U.S. PATENT DOCUMENTS

| | | | | |
|---|---|---|---|---|
| 1,501,919 | A | * | 7/1924 | Peters ........................ 83/659 |
| 4,841,712 | A | * | 6/1989 | Roou ........................ 53/412 |
| 5,352,722 | A | * | 10/1994 | Sweet et al. ............... 524/266 |
| 5,562,789 | A | * | 10/1996 | Hoffmann .................. 156/64 |
| 7,704,346 | B2 | * | 4/2010 | Cote ........................... 156/253 |

| | | | |
|---|---|---|---|
| 2004/0043062 | A1 | 3/2004 | Sun |
| 2006/0027044 | A1* | 2/2006 | Misaki ........................ 76/107.8 |
| 2008/0021421 | A1 | 1/2008 | Sun |

FOREIGN PATENT DOCUMENTS

| | | |
|---|---|---|
| CN | 1494901 A | 5/2004 |
| JP | 2001-269896 A | 10/2001 |
| JP | 2001269896 | * 10/2001 |
| JP | 2004-330364 A | 11/2004 |

OTHER PUBLICATIONS

Communication, dated Oct. 19, 2011, issued by the State Intellectual Property Office of P.R. China, in corresponding Chinese Application No. 200910159900.X.

* cited by examiner

*Primary Examiner* — Linda L Gray
(74) *Attorney, Agent, or Firm* — Sughrue Mion, PLLC (57) ABSTRACT

The invention provides a process for producing an adhesive patch, which includes a step of preparing a pressure-sensitive adhesive sheet including a backing, a pressure-sensitive adhesive layer formed on at least one side of the backing, and a release liner disposed on the pressure-sensitive adhesive layer; and a step of punching an adhesive patch including a backing, a pressure-sensitive adhesive layer formed on at least one side of the backing, and a release liner disposed on the pressure-sensitive adhesive layer out of the pressure-sensitive adhesive sheet with a protrudent push cutter blade, in which, at at least an edge part of the protrudent push cutter blade, a cross-sectional shape of the protrudent push cutter blade, which is in a direction perpendicular to the direction in which the protrudent push cutter blade extends, has an angle a and an angle b, in which the angle a is larger than the angle b. The angle a and angle b in the sectional shape have the meanings described in the specification.

9 Claims, 6 Drawing Sheets

FIG. 7E

PROCESS FOR PRODUCING ADHESIVE PATCH

FIELD OF THE INVENTION

The present invention relates to a process for producing an adhesive patch using a protrudent push cutter blade.

BACKGROUND OF THE INVENTION

Various adhesive patches have hitherto been developed for the purposes of, e.g., protecting the skin or administering a drug to the living body through the skin. Adhesive patches have a certain shape, e.g., a substantially rectangular shape. Such a shape can be obtained by firstly preparing a pressure-sensitive adhesive sheet in a web form and then cutting that shape out of this sheet with a cutter. Documents concerned with such cutters include JP-A-2001-269896 and JP-A-2004-330364. In general, cutters require special consideration in accordance with the physical and chemical properties of substances to be cut. In these documents, the substances to be cut are work materials such as metals and labels or the like, respectively. Those documents neither disclose nor suggest the cutting of adhesive patches such as those described above.

Incidentally, in adhesive patches, there are cases where the pressure-sensitive adhesive layer protrudes from the edge of the patch or the pressure-sensitive adhesive layer flows out during adhesive patch storage due to the so-called cold-flow phenomenon. In such cases, the pressure-sensitive adhesive layer which has protruded or flowed out may adhere to an inner surface of the package of the adhesive patch, making it difficult to easily take the adhesive patch out of the package, or the user may come to have a sticky hand and an uncomfortable feeling.

There is hence a desire for a process for producing an adhesive patch in which the pressure-sensitive adhesive layer can be inhibited from protruding from the edge of the adhesive patch or flowing out during adhesive patch storage, by cutting a piece having a certain shape out of a web-form pressure-sensitive adhesive sheet with a cutter.

SUMMARY OF THE INVENTION

In view of the problem described above, an object of the invention is to provide a process for producing an adhesive patch in which the pressure-sensitive adhesive can be inhibited from protruding or flowing out from the edge of the patch.

Surprisingly, such an object of the invention is accomplished with a production process including a step of punching an adhesive patch out of a pressure-sensitive adhesive sheet with a protrudent push cutter blade having a given sectional shape. Namely, the invention provides the following items.

1. A process for producing an adhesive patch, which comprises:
a step of preparing a pressure-sensitive adhesive sheet comprising a backing, a pressure-sensitive adhesive layer formed on at least one side of the backing, and a release liner disposed on the pressure-sensitive adhesive layer; and
a step of punching an adhesive patch comprising a backing, a pressure-sensitive adhesive layer formed on at least one side of the backing, and a release liner disposed on the pressure-sensitive adhesive layer out of the pressure-sensitive adhesive sheet with a protrudent push cutter blade,
wherein, at at least an edge part of the protrudent push cutter blade, a cross-sectional shape of the protrudent push cutter blade, which is in a direction perpendicular to the direction in which the protrudent push cutter blade extends, has an angle a and an angle b, in which the angle a is larger than the angle b,
wherein, in the cross-sectional shape, the angle a is an angle between a blade center line extending through a blade tip and a straight line corresponding to a side of the protrudent push cutter blade which faces the adhesive patch side, and
the angle b is an angle between the blade center line extending through the blade tip and a straight line corresponding to another side of the protrudent push cutter blade which does not face the adhesive patch side.

2. The process according to item 1, wherein the protrudent push cutter blade cuts the pressure-sensitive adhesive sheet from the backing side to the release liner side.

3. The process according to item 1 or 2, wherein the adhesive patch is punched out of the pressure-sensitive adhesive sheet with a die-cutting roll equipped with a die cutter having the protrudent push cutter blade and an anvil roll.

4. The process according to any one of items 1 to 3, wherein the angle a is 15 to 47.5 degrees.

5. The process according to any one of items 1 to 4, wherein at least a part of the edge of the pressure-sensitive adhesive layer of the adhesive patch is located on the adhesive patch center side with respect to either the edge of the backing or the edge of the release liner.

6. The process according to any one of items 1 to 5, wherein the angle b is 0 to 27.5 degrees.

7. The process according to any one of items 1 to 6, wherein the sum of the angle a and the angle b is 15 to 55 degrees.

8. The process according to any one of items 1 to 7, wherein the edge of the release liner of the adhesive patch is located on the adhesive patch periphery side with respect to a position on the release liner where a perpendicular segment drawn from the edge of the backing of the adhesive patch to the release liner intersects the release liner.

9. The process according to any one of items 1 to 8, wherein the pressure-sensitive adhesive layer contains an organic liquid ingredient.

10. The process according to any one of items 1 to 9, wherein the pressure-sensitive adhesive layer has a thickness of 100 μm or larger.

According to the production process of the invention, an adhesive patch in which at least a part of the edge of the pressure-sensitive adhesive layer is located at a given position on the adhesive patch center side can be easily produced without the necessity of conducting an additional step. In such an adhesive patch, the pressure-sensitive adhesive layer can be inhibited from protruding from the edge of the adhesive patch or flowing out during patch storage due to the so-called cold-flow phenomenon. The pressure-sensitive adhesive layer in such an adhesive patch is hence inhibited from adhering to the inner surface of the package of the adhesive patch. Consequently, the adhesive patch can be easily taken out of the package and the user is less apt to come to have a sticky hand and an uncomfortable feeling.

In the adhesive patch according to the production process of the invention, the edge of the pressure-sensitive adhesive layer is exposed. Namely, the edge of the pressure-sensitive adhesive layer is covered with neither an edge of the backing nor an edge of the release liner. This coupled with the constitution described above, in which the pressure-sensitive adhesive layer is inhibited from protruding or flowing out and use of the adhesive patch is hence less apt to result in a sticky hand, enables the user to exceedingly easily pinch the edge of the release liner with fingers to peel off the release liner when the adhesive patch of the invention is used.

As described above, an adhesive patch which is comfortably usable can be easily produced by the process of the invention.

DESCRIPTION OF REFERENCE NUMERALS AND SIGNS

| | |
|---|---|
| 11 | Pressure-sensitive adhesive sheet |
| 12 | Backing |
| 13 | Pressure-sensitive adhesive layer |
| 14 | Release liner |
| 15 | Adhesive patch |
| 21 | Pressure-sensitive adhesive sheet |
| 22 | Backing |
| 23 | Pressure-sensitive adhesive layer |
| 24 | Release liner |
| 26 | Protrudent push cutter blade |
| 27 | Direction facing adhesive patch |
| 28 | Direction not facing adhesive patch |
| 29 | Hard table |
| 210 | Cutting direction |
| 211 | Blade center line |
| 32 | Backing |
| 33 | Pressure-sensitive adhesive layer |
| 34 | Release liner |
| 35 | Adhesive patch |
| 41 | Pressure-sensitive adhesive sheet |
| 46 | Protrudent push cutter blade |
| 47 | Die cutter |
| 48 | Anvil roll |
| 412 | Axis of rotation of anvil roll |
| 52 | Backing |
| 53 | Pressure-sensitive adhesive layer |
| 54 | Release liner |
| 55 | Adhesive patch |
| 59 | Perpendicular segment drawn to release liner |
| 513 | Projecting part |
| 514 | Segment connecting edge of release liner to edge of backing |

DETAILED DESCRIPTION OF THE INVENTION

Preferred embodiments of the invention are shown below. However, the following detailed explanations thereon, drawings, and specific examples are intended only for exemplification and should not limit the scope of the invention. The following explanations on preferred embodiments are merely illustrative and are never intended to limit the invention and the applications or uses thereof In the drawings, the members or parts do not always coincide in size, proportion, or shape with ones to be used in actual production, for an easy understanding of the concept of the invention.

The process for producing adhesive patch according to the invention includes a step of preparing a pressure-sensitive adhesive sheet and a step of punching an adhesive patch out of the pressure-sensitive adhesive sheet with a protrudent push cutter blade.

Figure 1:
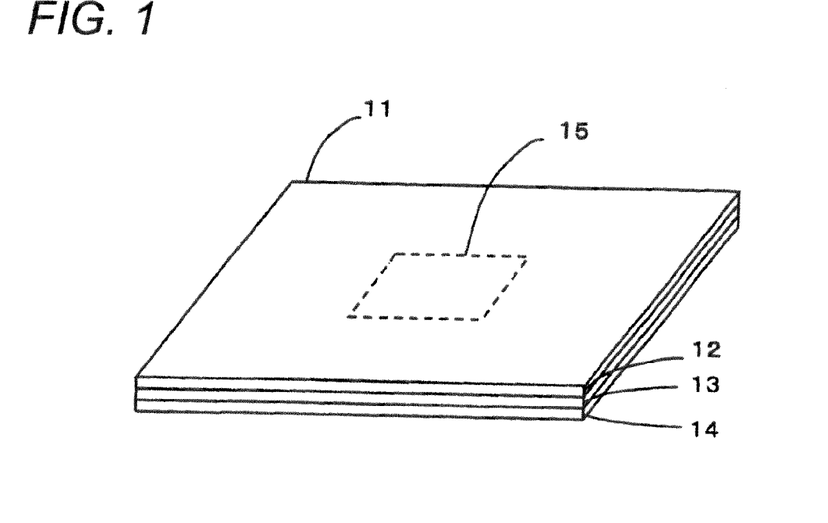
FIG. 1 is a diagrammatic view illustrating an embodiment of a step of preparing a pressure-sensitive adhesive sheet.

FIG. 1 is a diagrammatic slant view illustrating the step of preparing a pressure-sensitive adhesive sheet 11, which includes a backing 12, a pressure-sensitive adhesive layer 13 formed on at least one side of the backing 12, and a release liner 14 disposed on the pressure-sensitive adhesive layer 13. This step is followed by the step of punching an adhesive patch 15 having a certain shape, e.g., a substantially rectangular shape such as that indicated by the broken lines, out of the pressure-sensitive adhesive sheet 11.

Figure 2A:
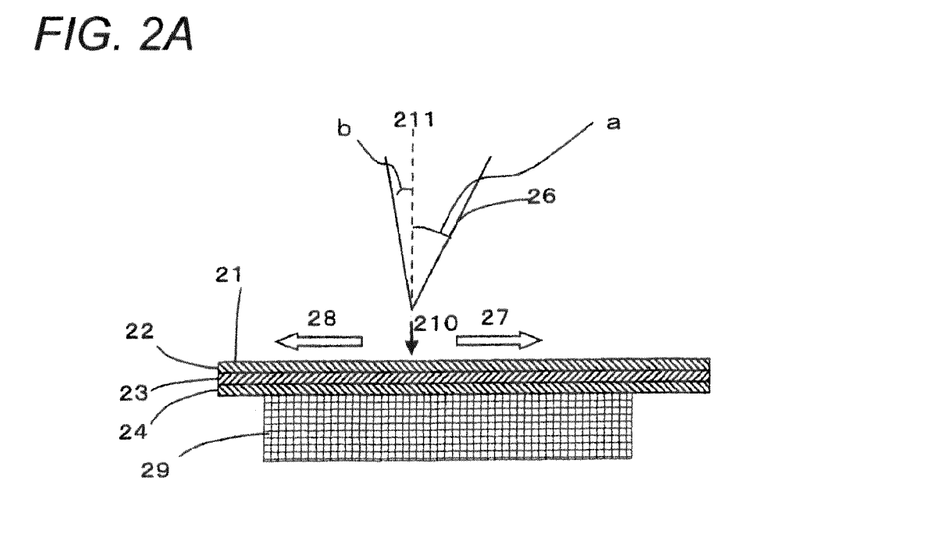
FIG. 2A is a diagrammatic view illustrating an embodiment of a step of punching an adhesive patch out of a pressure-sensitive adhesive sheet with a protrudent push cutter blade.

FIG. 2A diagrammatically illustrates the step of punching an adhesive patch out of a pressure-sensitive adhesive sheet 21, by means of a sectional view of a plane perpendicular to the direction in which a protrudent push cutter blade 26 extends. As shown in the sectional view given in FIG. 2A, at least an edge part of the protrudent push cutter blade 26 has such a cross-sectional shape that an angle a is larger than an angle b. In the cross-sectional shape, angle a is the angle between the straight line corresponding to that side of the protrudent push cutter blade 26 which faces in the direction 27 facing the adhesive patch and the blade center line 211 which passes through the blade tip and corresponds to the cutting direction 210 for the protrudent push cutter blade. Hereinafter, this angle is referred to as patch-side angle a. In the sectional shape, angle b is the angle between the straight line corresponding to that side of the protrudent push cutter blade 26 which faces in the direction 28 not facing the adhesive patch and the blade center line 211 which passes through the blade tip and corresponds to the cutting direction 210 for the protrudent push cutter blade. Hereinafter, this angle is referred to as non-patch-side angle b. The cutting direction 210 and the blade center line 211 are usually approximately perpendicular to the pressure-sensitive adhesive sheet 21. Namely, the angle between the pressure-sensitive adhesive sheet 21 and each of the cutting direction 210 and the blade center line 211 is usually 70 to 110 degrees.

The patch-side angle a is larger than the non-patch-side angle b as described above. Accordingly, when the protrudent push cutter blade 26 is used to cut the pressure-sensitive adhesive sheet 21 for producing an adhesive patch, the cutter blade 26 works so as to push the pressure-sensitive adhesive layer 23 of the pressure-sensitive adhesive sheet 21 toward the adhesive patch center side. As a result, in the edge, specifically the lateral edge, of the adhesive patch produced, at least a part of the edge, specifically the lateral edge, of the pressure-sensitive adhesive layer 23 is preferably located on the adhesive patch center side.

Figure 2B:
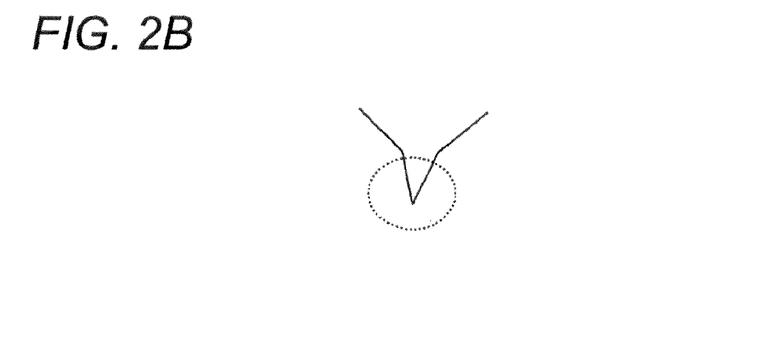
FIG. 2B is a diagrammatic view illustrating an embodiment of a cross-sectional shape of a protrudent push cutter blade.

The protrudent push cutter blade 26 is not particularly limited so long as the edge part thereof has such a cross-sectional shape as described above. For example, the part other than the edge part (surrounded by the broken-line circle) may have a thicker cross-sectional shape as shown in FIG. 2B. As shown in FIG. 2A, this step preferably includes disposing the pressure-sensitive adhesive sheet 21 on a hard table 29, e.g., an anvil roll, and push-cutting the pressure-sensitive adhesive sheet 21 with the protrudent push cutter blade 26 to punch an adhesive patch out of the pressure-sensitive adhesive sheet 21.

Figure 3A:
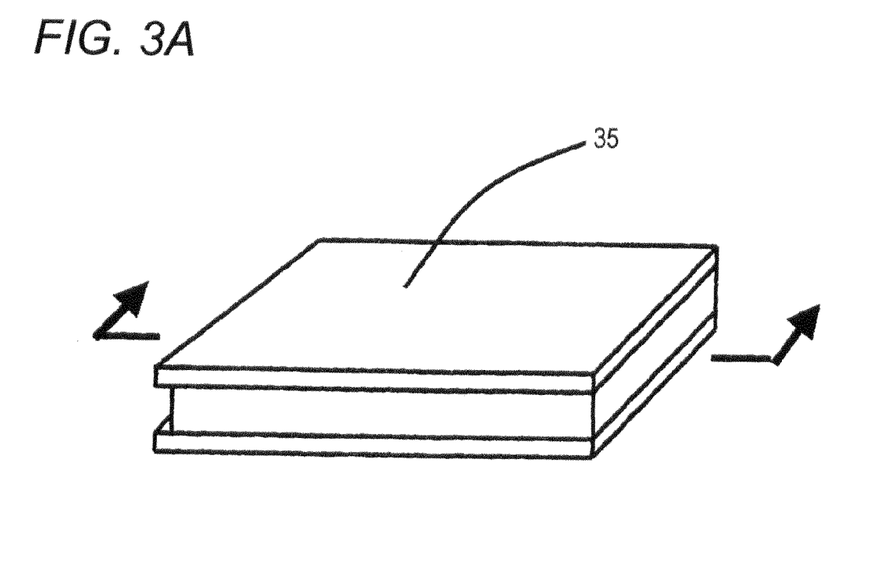
FIGS. 3A and 3B are diagrammatic views illustrating an embodiment of an adhesive patch obtained by the production process of the invention.
Figure 3B:
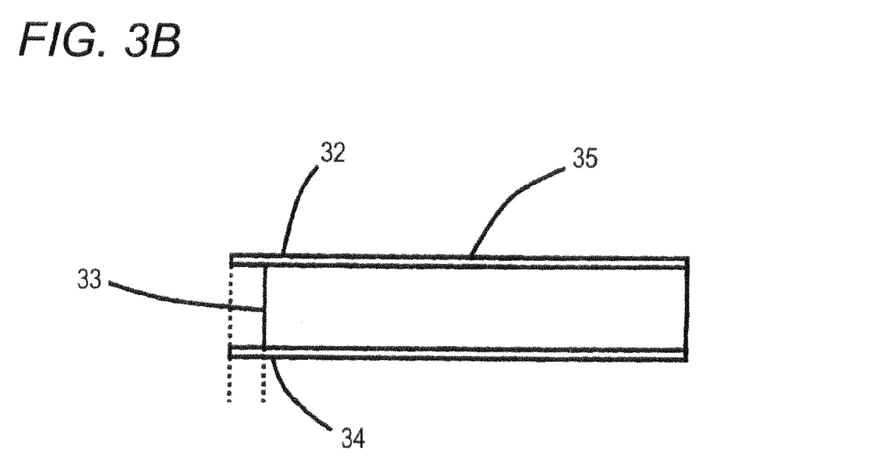

FIGS. 3A and 3B are diagrammatic views of a preferred adhesive patch 35 obtained by the production process of the invention. FIG. 3A is a diagrammatic slant view thereof, and FIG. 3B is a diagrammatic sectional view thereof taken in the direction of the arrows. With reference to FIG. 3A, the shape of this adhesive patch 35 is not particularly limited. For example, this adhesive patch 35 has a substantially planar sheet form, and the planar shape thereof is substantially rectangular. Although the size thereof is not particularly limited, a specific embodiment has a shape in which one side has a length of about 20 to 80 mm and another side has a length of about 20 to 80 mm. Other planar shapes are possible, such as substantially polygonal shapes including substantially triangular shapes and substantially pentagonal shapes, substantially elliptic shapes, substantially circular shapes, and indefinite shapes.

As shown in FIGS. 3A and 3B and as stated above, at least a part of the edge of the pressure-sensitive adhesive layer 33 of the adhesive patch 35 obtained by the production process of the invention is preferably located on the adhesive patch 35 center side with respect to either the edge of the backing 32 or the edge of the release liner 34. This constitution enables the edge of the pressure-sensitive adhesive layer 33 to be less apt to protrude or flow out from the edge of the adhesive patch 35.

As shown in FIGS. 3A and 3B, at the edge of the adhesive patch 35 obtained by the production process of the invention, the edge of the pressure-sensitive adhesive layer 33 is preferably exposed, i.e., is not covered with the edge of the backing 32 and/or the edge of the release liner 34. According to this constitution, when the user pinches the edge of the release liner 34 with fingers to peel off the release liner 34, areas suitable for pinching are easily obtained. As a result, the release liner 34 can be easily peeled off.

The thickness of the backing is preferably 15 to 150 μm, more preferably 20 to 100 μm. When the thickness thereof is 15 μm or larger, the pressure-sensitive adhesive which has protruded or flowed out from the edge of the pressure-sensitive adhesive layer is sufficiently inhibited from moving to that surface of the backing which is opposite to the pressure-sensitive adhesive layer. When the thickness thereof is 150 μm or smaller, the adhesive patch can be sufficiently inhibited from giving a stiff feeling during wear.

The thickness of the pressure-sensitive adhesive layer is advantageously 100 μm or larger, more advantageously 100 to 300 μm. Usually, when a pressure-sensitive adhesive layer has a thickness of 100 μm or larger, such a pressure-sensitive adhesive layer tends to readily protrude or flow out from the edge of the adhesive patch. However, since the edge of the adhesive patch obtained by the production process of the invention preferably has the shape described above, even the pressure-sensitive adhesive layer having such a thickness can be effectively inhibited from protruding or flowing out. When the thickness of the pressure-sensitive adhesive layer is 300 μm or smaller, the shape of the pressure-sensitive adhesive layer is retained more satisfactorily and the pressure-sensitive adhesive layer having such a thickness can be inhibited from protruding or flowing out.

With reference to FIGS. 3A and 3B, the edge of the pressure-sensitive adhesive layer 33 has a substantially linear cross-sectional shape. However, the shape thereof should not be construed as being limited to linear ones. The cross-sectional shape thereof may be, for example, a curved shape such as a curved shape protrudent toward the adhesive patch center side or edge side, a wavy shape, a zigzag shape, or the like. A curved shape is preferred because the pressure-sensitive adhesive layer is less apt to flow out.

After the adhesive patch is applied, the backing is used as part of the adhesive patch main body, i.e., as part of the pressure-sensitive adhesive layer and backing, during wear on the skin. On the other hand, the release liner, before application to the skin, ensures the stiffness of the adhesive patch to ensure the handleability of the adhesive patch. However, the release liner is usually discarded before the adhesive patch is applied to the skin. It is therefore preferred, from the standpoint of inhibiting the adhesive patch from giving an uncomfortable feeling during wear on the skin, that the backing should be softer than the release liner. From this standpoint, the thickness of the release liner is preferably 200 to 1,000 μm.

With reference to FIG. 2A again, it is preferred that the protrudent push cutter blade 26 cut the pressure-sensitive adhesive sheet 21 from the backing 22 side to the release liner 24 side as in this embodiment. Since the backing 22 is preferably softer than the release liner 24, the stress applied to the pressure-sensitive adhesive sheet 21 from the protrudent push cutter blade 26 is efficiently transmitted through the backing 22 to the pressure-sensitive adhesive layer 23. Consequently, when the protrudent push cutter blade 26 cuts the pressure-sensitive adhesive sheet 21 in producing an adhesive patch, the protrudent push cutter blade 26 can sufficiently push the edge of the pressure-sensitive adhesive layer 23 of the pressure-sensitive adhesive sheet 21 toward the adhesive patch center side. In this specification, the softness of the backing and that of the release liner 24 are ones determined by Japanese Industrial Standards "JIS L1085 5.7, Method A of Bending Resistance (45° cantilever method)".

With reference to FIG. 2A, from the standpoint of enabling the protrudent push cutter blade 26 to sufficiently push the edge of the pressure-sensitive adhesive layer of the pressure-sensitive adhesive sheet 21 toward the adhesive patch center side, the angle a is preferably 15 to 47.5 degrees, more preferably 37.5 to 47.5 degrees. In case where the angle a is smaller than 15 degrees, it is difficult to sufficiently push the edge of the pressure-sensitive adhesive layer in the edge of the adhesive patch toward the adhesive patch center side. On the other hand, in case where the angle a exceeds 47.5 degrees, this protrudent push cutter blade might have reduced cutting quality and it is necessary to take account of the possibility of resulting in a reduced efficiency of punching out.

With reference to FIG. 2A, the sum of the angle a and the angle b is preferably 15 to 55 degrees, more preferably 20 to 50 degrees. In case where the sum of the angles is smaller than 15 degrees, it is necessary to take account of the possibility that this protrudent push cutter blade might have reduced durability and reduced punching ability. On the other hand, in case where the sum of the angles exceeds 55 degrees, it is necessary to take account of the possibility that this protrudent push cutter blade might have reduced cutting quality and reduced punching ability.

The angle b is preferably 0 to 27.5 degrees, more preferably 2.5 to 27.5 degrees. Protrudent push cutter blade having an angle b smaller than 0 degree is difficult to produce. On the other hand, in case where the angle b exceeds 27.5 degrees, it is necessary to take account of the possibility of resulting in reduced punching ability. In the case where a protrudent push cutter blade having a substantially rectangular planar shape along the direction in which the blade extends is used for punching out the pressure-sensitive adhesive sheet, the edge part of this protrudent push cutter blade preferably has an angle b of 7.5 degrees or smaller from the standpoint of punching out the pressure-sensitive adhesive sheet without fail.

Figure 4:
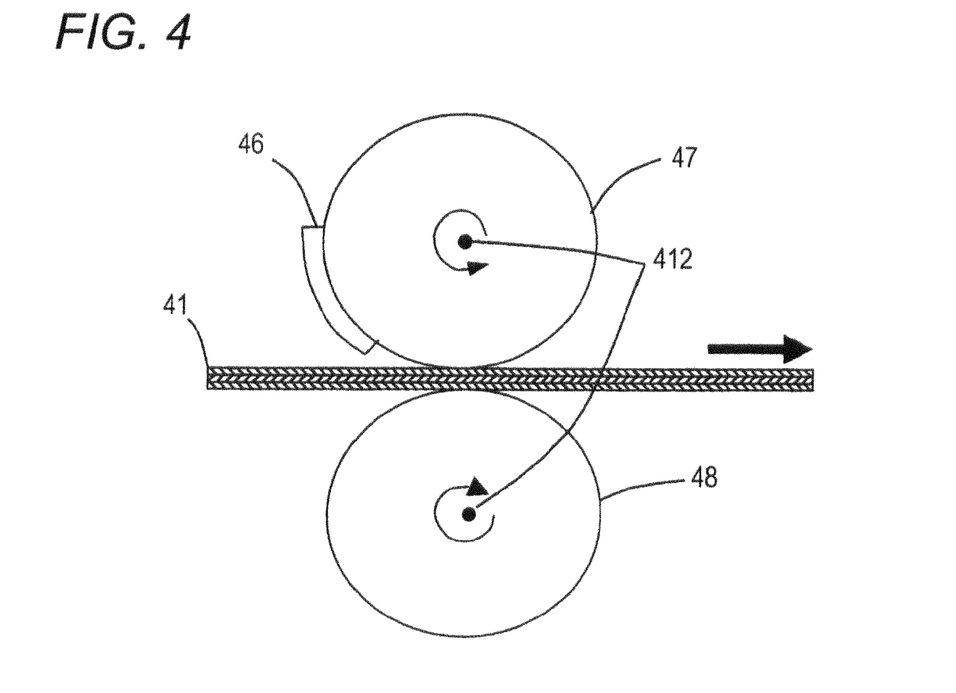
FIG. 4 is a diagrammatic view illustrating an embodiment of the step of punching an adhesive patch out of a pressure-sensitive adhesive sheet with a die-cutting roll.

With reference to FIG. 4, FIG. 4 diagrammatically illustrates the step of punching the adhesive patch out of a pressure-sensitive adhesive sheet 41 with a die-cutting roll including a die cutter 47 having the protrudent push cutter blade 46 and an anvil roll 48. This drawing diagrammatically shows a section along a plane perpendicular to the axes of rotation 412 of the die cutter and anvil roll. The pressure-sensitive adhesive sheet runs in the direction of the arrow over the anvil roll rotating in the arrow direction. The protrudent push cutter blade 46 of the die cutter 47 rotating in the arrow direction punches an adhesive patch out of the pressure-sensitive adhesive sheet 41. With the die-cutting roll having such constitution, the cutting step can be rapidly conducted continuously. This die-cutting roll is hence advantageous in the industrial production of adhesive patches.

Figure 5:
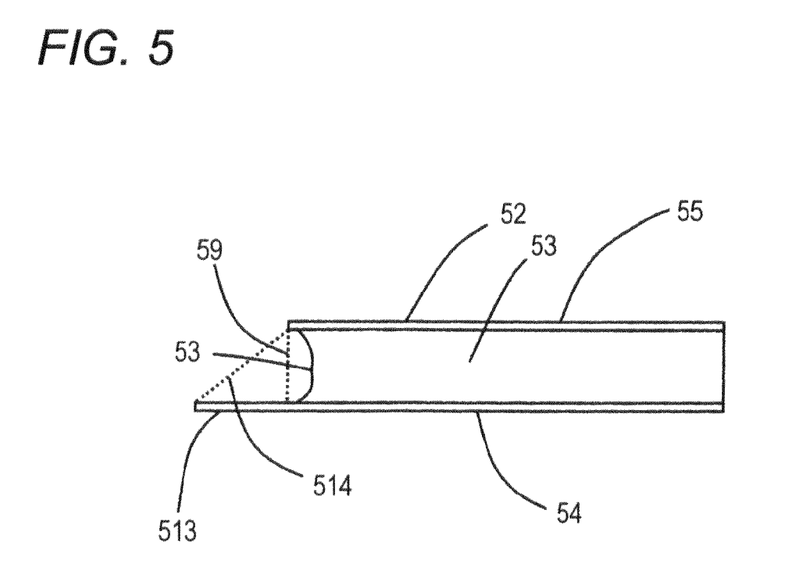
FIG. 5 is a diagrammatic view illustrating another embodiment of an adhesive patch obtained by the production process of the invention.

FIG. 5 shows a diagrammatic sectional view of the edge of an adhesive patch 55 to be punched out. Like the adhesive patch 35 shown in FIG. 3, in the adhesive patch 55 shown in FIG. 5, at least a part of the edge of the pressure-sensitive adhesive layer 53 is located on the adhesive patch 55 center side with respect to either the edge, specifically the lateral edge, of the backing 52 or the edge, specifically the lateral edge, of the release liner 54. The edge of the release liner 54 of the adhesive patch 55 shown in FIG. 5 is located on the adhesive patch 55 periphery side with respect to a position on the release liner 54 where a perpendicular segment 59 drawn from the edge of the backing 52 of the adhesive patch 55 to the release liner 54 intersects the release liner 54. In this embodiment, the release liner 54 has a projecting part 513 which projects toward the adhesive patch 55 periphery side from the position on the release liner 54 where a perpendicular segment 59 drawn from the edge of the backing 52 of the adhesive patch 55 to the release liner 54 intersects the release liner 54. Even when the pressure-sensitive adhesive layer 53 of the adhesive patch 55 having such constitution protrudes from the edge of the adhesive patch 55, the space located on the adhesive patch center side of the segment 514 indicated by a broken line, which connects the edge of the release liner 54 to the edge of the backing 52, can inhibit the pressure-sensitive adhesive layer 53 from coming into contact with the inner wall of the package of the adhesive patch 55. Consequently, this adhesive patch is superior in that the adhesive patch is less apt to adhere to the package.

Such an adhesive patch can be easily obtained by the production process of the invention. Namely, the protrudent push cutter blade is moved from the backing side toward the release liner and the push-cutting is stopped at the moment when the cutter blade comes into contact with the release liner, whereby the target adhesive patch can be obtained.

In the process for adhesive patch production of the invention described above, the backing is not particularly limited, and a known material in a film or sheet form may be used. Such a backing preferably is one which is substantially impermeable to components of the pressure-sensitive adhesive layer, such as a drug and additives, and prevents the components from passing through the backing and evaporating off from the back to cause a decrease in content.

Examples of such backings include single-layer films of polyesters such as poly(ethylene terephthalate), nylons, Saran (registered trademark), polyethylene, polypropylene, poly(vinyl chloride), ethylene/ethyl acrylate copolymers, polytetrafluoroethylene, Surlyn (registered trademark), and metal foils and laminated films composed of two or more thereof.

The pressure-sensitive adhesive layer is not particularly limited. Examples of the pressure-sensitive adhesive include acrylic pressure-sensitive adhesives containing an acrylic polymer; rubber-based pressure-sensitive adhesives such as styrene/diene/styrene block copolymers (e.g., styrene/isoprene/styrene block copolymers and styrene/butadiene/styrene block copolymers), polyisoprene, polyisobutylene, and polybutadiene; silicone type pressure-sensitive adhesives such as silicone rubbers, dimethylsiloxane-based polymers, and diphenylsiloxane-based polymers; vinyl ether type pressure-sensitive adhesives such as poly(vinyl methyl ether), poly(vinyl ethyl ether), and poly(vinyl isobutyl ether); vinyl ester type pressure-sensitive adhesives such as vinyl acetate/ethylene copolymers; and polyester type pressure-sensitive adhesives produced from a carboxylic acid ingredient such as dimethyl terephthalate, dimethyl isophthalate, or dimethyl phthalate and a polyhydric alcohol ingredient such as ethylene glycol. The pressure-sensitive adhesive layer may be either a crosslinked pressure-sensitive adhesive layer or an uncrosslinked pressure-sensitive adhesive layer. From the standpoint of adhesion to the skin, hydrophobic pressure-sensitive adhesives are preferred and pressure-sensitive adhesive layers containing no water are preferred.

Of those pressure-sensitive adhesives, the rubber-based pressure-sensitive adhesives tend to give a pressure-sensitive adhesive layer which is apt to protrude or flow out. Since the invention can effectively inhibit such protrusion or outflow, the invention is especially advantageous in the case where a rubber-based pressure-sensitive adhesive is used for the pressure-sensitive adhesive layer. For the same reason, the invention is advantageous to uncrosslinked pressure-sensitive adhesive layers.

A mixture of rubber-based pressure-sensitive adhesives which are constituted of the same component(s) or different components and differ from each other in average molecular weight can be used in order to obtain moderate adhesive force and drug solubility. For example, when polyisobutylenes are employed as an example, it is preferred to use a mixture of high-molecular polyisobutylene having a viscosity-average molecular weight of 1,800,000 to 5,500,000 with medium-molecular polyisobutylene having a viscosity-average molecular weight of 40,000 to 85,000 and optionally with low-molecular polyisobutylene.

In this case, it is preferred that the high-molecular polyisobutylene be incorporated in a proportion of 10 to 80% by weight, preferably 10 to 50% by weight, the medium-molecular polyisobutylene be incorporated in a proportion of 0 to 90% by weight, preferably 10 to 80% by weight, and the low-molecular polyisobutylene be incorporated in a proportion of 0 to 80% by weight, preferably 0 to 60% by weight. The term "viscosity-average molecular weight" herein means the viscosity-average molecular weight calculated with the Flory's viscosity equation.

A tackifier such as rosin resin, polyterpene resin, coumarone-indene resin, petroleum resin, terpene-phenol resin, or xylene resin may be incorporated in rubber-based pressure-sensitive adhesives in order to impart moderate tackiness. Such tackifiers may be used alone or as a mixture of two or more thereof. The content of the tackifier in the pressure-sensitive adhesive layer is, for example, 10 to 40% by weight.

The pressure-sensitive adhesive layer may contain a drug according to need, whereby a patch preparation can be provided. The drug herein is not particularly limited. Preferred is a drug which can be administered to a mammal such as a human being through the skin, i.e., which is percutaneously absorbable. The drug can be incorporated into the pressure-sensitive adhesive layer in an amount of, e.g., 0.1 to 50% by weight.

The organic liquid ingredient is not particularly limited. Examples thereof include glycols such as ethylene glycol, diethylene glycol, propylene glycol, dipropylene glycol, tripropylene glycol, triethylene glycol, polyethylene glycol, and polypropylene glycol; fats and oils such as olive oil, castor oil, and lanolin; hydrocarbons such as squalane and liquid paraffin; various surfactants; ethoxy stearyl alcohol; glycerol monoesters such as oleic acid monoglyceride, caprylic acid monoglyceride, and lauric acid monoglyceride, glycerol diesters such as polypropylene (in general, polyalkylene) glycol dialkyl esters, glycerol triesters such as glycerol triacetate, and mixtures thereof; alkyl esters of fatty acids, such as triethyl citrate; higher alcohols; higher fatty acids such as oleic acid and caprylic acid; pyrrolidone compounds such as N-methylpyrrolidone and N-dodecylpyrrolidone; sulfoxides such as decyl methyl sulfoxide; and 1,3-butanediol. These ingredients may be used alone or as a mixture of two or more thereof. The organic liquid ingredient can be incorporated in an amount of preferably 10 to 60% by weight, more preferably 15 to 60% by weight, and most preferably 20 to 60% by weight, based on the whole pressure-sensitive adhesive layer. When a pressure-sensitive adhesive layer contains such an organic liquid ingredient in an amount of 10% by weight or larger, this pressure-sensitive adhesive layer is apt to be plasticized and to protrude or flow out. Since the invention can effectively inhibit this protrusion or outflow, the invention is advantageous in such a case. Incidentally, in case where an organic liquid ingredient is contained in an amount exceeding 60% by weight, there is a possibility that it is difficult for the pressure-sensitive adhesive layer to retain a given shape.

The release liner is not particularly limited. Examples of the material thereof include materials which are known in this field. Specific examples thereof include films of plastics such as polyesters including poly(ethylene terephthalate), poly(vinyl chloride), poly(vinylidene chloride), various acrylic and methacrylic polymers, polystyrene, polycarbonates, polyimides, cellulose acetate (acetate), regenerated cellulose (cellophane), and celluloid and laminated films composed of wood-free paper, glassine paper, or the like and a polyolefin. From the standpoints of safety, profitability, and drug migration prevention, it is preferred to use a polyester film. The release liner preferably is one in which the side facing the pressure-sensitive adhesive layer has undergone a releasant treatment so as to facilitate peeling from the pressure-sensitive adhesive layer. In this specification, the evaluation values concerning cross-sectional shapes of adhesive patches mean values obtained by the methods described in the Examples.

EXAMPLES

The invention will be explained below in more detail by reference to Examples, but the invention should not be construed as being limited to the following Examples.

(1) Production of Pressure-Sensitive Adhesive Sheet
Preparation of Coating Fluid
The following ingredients were weighed out: 6.250 kg of toluene, 8.750 kg of n-hexane, and 1.043 kg of high-molecular polyisobutylene (viscosity-average molecular weight, 4,000,000). These ingredients were stirred together by means of a mixing tank for 24 hours or more. Thereafter, 2.087 kg of medium-molecular polyisobutylene (viscosity-average molecular weight, 55,000), 2.087 kg of an alicyclic saturated hydrocarbon resin, and 0.500 kg of toluene were weighed out and introduced into the mixing tank. The resultant mixture was stirred for 24 hours or more. Thereafter, 2.282 kg of isopropyl myristate and 2.000 kg of toluene were weighed out and introduced into the mixing tank. This mixture was stirred for 4 hours or more to obtain a coating fluid.

Preparation of Pressure-Sensitive Adhesive Sheet
The coating fluid was applied to the lightly peelable side of 75 μm-thick poly(ethylene terephthalate) (hereinafter referred to as "PET") as a release liner with a coater including a back-up roll and a comma roll in such an amount as to result in a pressure-sensitive adhesive layer thickness of 160 μm on a dry basis. The coating fluid applied was dried. The pressure-sensitive adhesive side of the resultant coated release liner was press-bonded to the PET nonwoven fabric side of a PET film/PET nonwoven fabric laminate as a backing. Thus, a pressure-sensitive adhesive sheet was obtained.

(2) Production of Adhesive Patch with Die Cutter
Test 1 and Test 2 were conducted to punch adhesive patch samples out of the pressure-sensitive adhesive sheet with a die-cutting roll including a die cutter having a protrudent push cutter blade and an anvil roll. The cross-sectional shapes of edge parts of the protrudent push cutter blades used in Test 1 (Examples 1 to 4 and Comparative Examples 1 to 5) are shown in FIGS. 6A to 6I, the cross-sections each being perpendicular to the direction in which the blade extends. In Test 1, use was made of a die-cutting roll having a straight protrudent push cutter blade extending perpendicularly to the direction of the running of the pressure-sensitive adhesive sheet. In Test 2 (Examples 5 to 9 and Comparative Example 6), use was made of a die-cutting roll having a protrudent push cutter blade in which an edge part thereof had a substantially rectangular planar shape along the direction in which the blade extended.

The pressure-sensitive adhesive sheet was disposed so that the backing side thereof faced the anvil roll side and the release liner side thereof faced the die cutter side. The pressure-sensitive adhesive sheet was cut to obtain adhesive patches of Examples 1 to 8 and Comparative Examples 1 to 6. In this cutting, punching ability was also evaluated according to the following evaluation criteria.

(3) Test Methods
Punching Ability
Immediately after each adhesive patch was punched out of the pressure-sensitive adhesive sheet, punching ability was visually evaluated according to the following criteria.
Good: Patches are normally punched out.
Fair: Punching failure occurs occasionally.
Poor: Most of the punching operations result in failure.
Protrusion of Pressure-Sensitive Adhesive Layer
A. A razor blade, a wood hammer, and an acrylic plate were prepared.
B. An adhesive patch was placed on the acrylic plate. The razor blade was perpendicularly applied to the surface of the backing of the adhesive patch and struck once with the wood hammer to cut the patch into a substantially square shape having a length of 2 cm and a width of 2 cm. Thus, five samples were produced for each of the Examples and Comparative Examples.
C. The sectional shape of each sample was examined with a digital microscope (VHX500, manufactured by Keyence Corp.) (magnification, 500 diameters) and evaluated according to the following criteria. In Test 2, photographs of the sectional shapes were also taken.
Excellent: The pressure-sensitive adhesive layer is located sufficiently on the inner side of the perpendicular segment drawn from the edge of the backing to the liner.

Good: The pressure-sensitive adhesive layer is located on the inner side of the perpendicular segment drawn from the edge of the backing to the liner.

Fair: The edge of the pressure-sensitive adhesive layer is located on the perpendicular segment drawn from the edge of the backing to the liner.

Poor: The edge of the pressure-sensitive adhesive layer is located on the outer side of the perpendicular segment drawn from the edge of the backing to the liner.

Results of Test 1 are shown in Table 1, and results of Test 2 are shown in Table 2 and FIGS. 7A to 7E.

TABLE 1

Figure 6A:
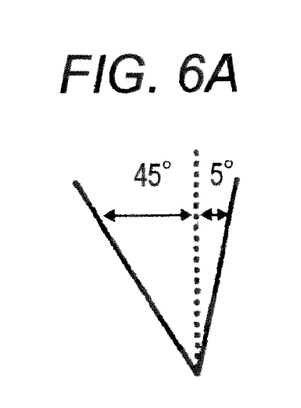
FIGS. 6A to 6I are diagrammatic views illustrating sectional shapes of the protrudent push cutter blades used in Examples 1 to 4 and Comparative Examples 1 to 5.
Figures 6B, 6F:
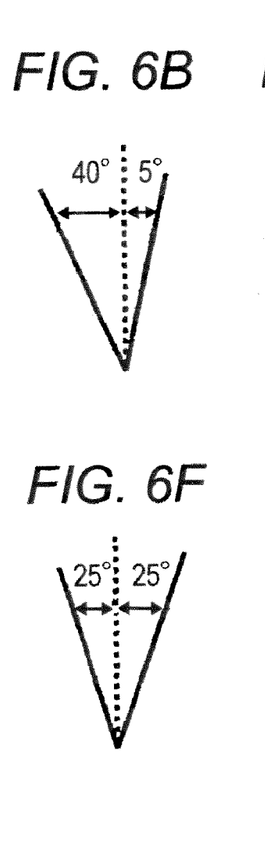
Figure 6C:
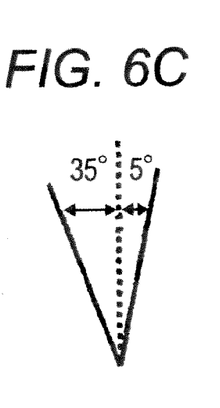
Figure 6D:
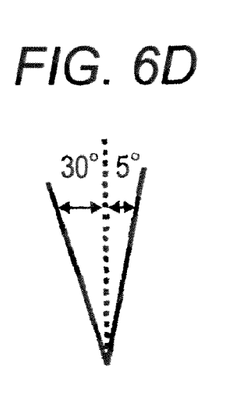
Figure 6E:
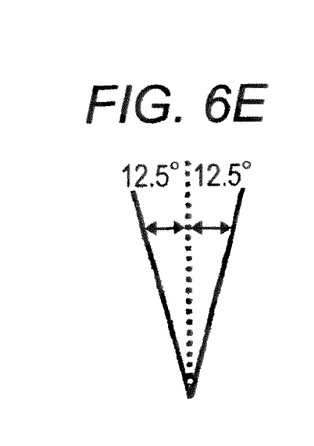
Figure 6G:
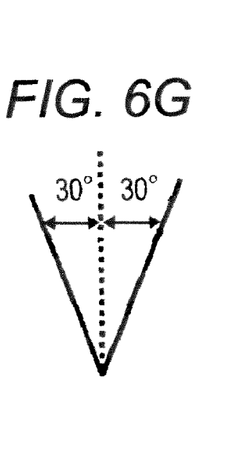
Figure 6H:
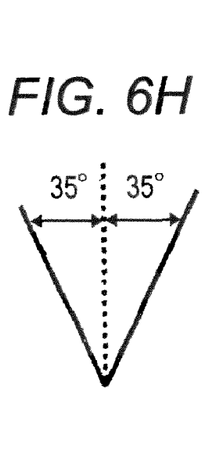
Figure 6I:
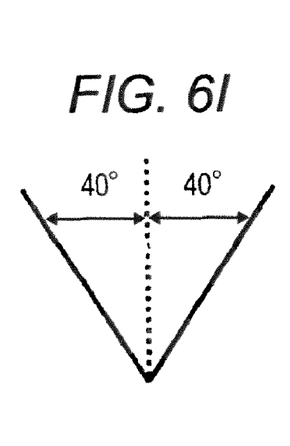

| | Sectional shape of push cutter blade (patch-side angle a/ non-patch-side angle b) | Angel a + angle b | Punching ability | Sectional shape | Sectional shape of blade edge |
|---|---|---|---|---|---|
| Example 1 | 45°/5° | 50° | fair | excellent | FIG. 6A |
| Example 2 | 40°/5° | 45° | good | excellent | FIG. 6B |
| Example 3 | 35°/5° | 40° | good | good | FIG. 6C |
| Example 4 | 30°/5° | 35° | good | good | FIG. 6D |
| Comparative Example 1 | 12.5°/12.5° | 25° | good | poor | FIG. 6E |
| Comparative Example 2 | 25°/25° | 50° | good | fair | FIG. 6F |
| Comparative Example 3 | 30°/30° | 60° | fair | good | FIG. 6G |
| Comparative Example 4 | 35°/35° | 70° | fair | good | FIG. 6H |
| Comparative Example 5 | 40°/40° | 80° | fair | good | FIG. 6I |

TABLE 2

Figure 7A:
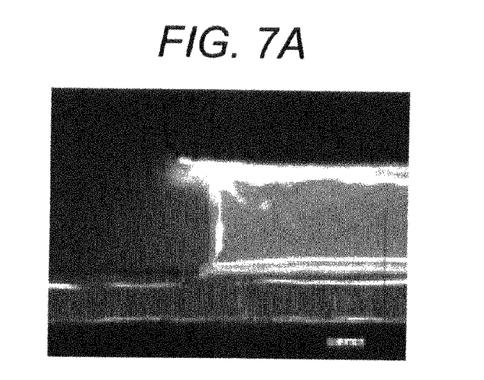
FIGS. 7A to 7E are photographs of sections of the adhesive patches obtained by the production processes of Examples 5 to 8 and Comparative Example 6.
Figure 7B:
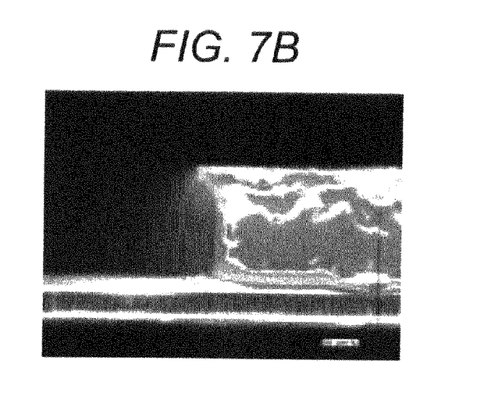
Figure 7C:
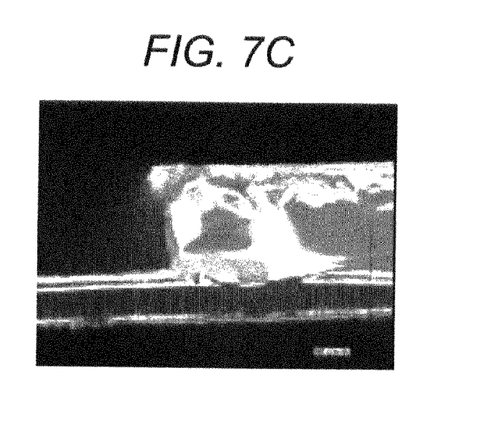
Figure 7D:
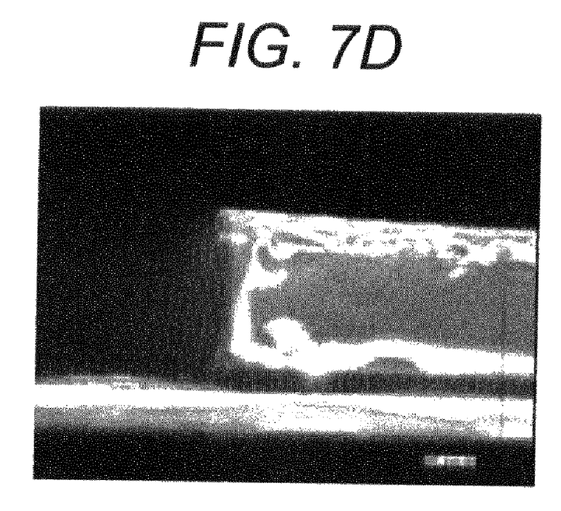
Figure 7E:
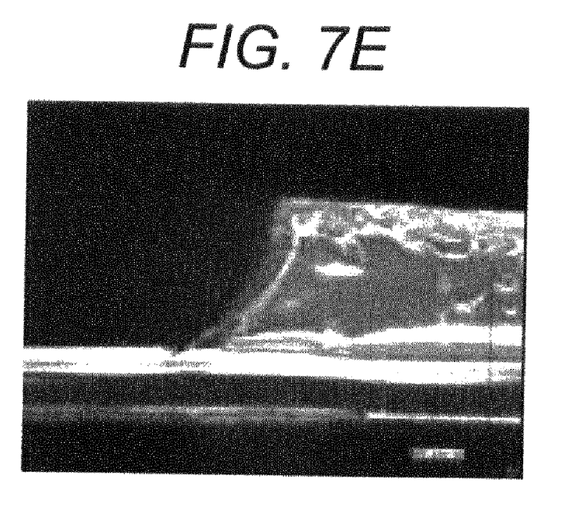

| | Sectional shape of push cutter blade (patch-side angle a/non-patch-side angle b) | Angel a + angle b | Punching ability | Sectional shape | Photograph |
|---|---|---|---|---|---|
| Example 5 | 45°/5° | 50° | fair | excellent | FIG. 7A |
| Example 6 | 40°/5° | 45° | good | excellent | FIG. 7B |
| Example 7 | 35°/5° | 40° | good | good | FIG. 7C |
| Example 8 | 25°/5° | 30° | good | good | FIG. 7D |
| Comparative Example 6 | 12.5°/12.5° | 25° | good | fair | FIG. 7E |

Table 1 and Table 2 show the followings. In the Examples, which employed protrudent push cutter blades in which the patch-side angle a was larger than the non-patch-side angle b, the edge of the pressure-sensitive adhesive layer was able to be pushed toward the adhesive patch center side. The edges of the adhesive patches obtained in the Examples had a preferred sectional shape. In the Examples, punching ability also was satisfactory. Consequently, in the Examples, the trouble that the edge of an adhesive patch becomes tacky or the pressure-sensitive adhesive layer protrudes was able to be more diminished from just after production than in conventional adhesive patches. In contrast, in the Comparative Examples, which employed protrudent push cutter blades in which the patch-side angle a was equal to the non-patch-side angle b, the cutter blades showed poor punching ability or gave an undesirable sectional shape.

The explanations on the invention are merely illustrative, and modifications of the invention which do not depart from the spirit of the invention are intended to be within the scope of the invention. Such modifications should not be construed as departing from the spirit and scope of the invention.

This application is based on Japanese patent application No. 2008-184670 filed on Jul. 16, 2008, the entire contents thereof being hereby incorporated by reference.

What is claimed is:

1. A process for producing an adhesive patch, which comprises:

a step of preparing a pressure-sensitive adhesive sheet comprising a backing, a pressure-sensitive adhesive layer formed on at least one side of the backing, and a release liner disposed on the pressure-sensitive adhesive layer; and a step of punching an adhesive patch comprising a backing, a pressure-sensitive adhesive layer formed on at least one side of the backing, and a release liner disposed on the pressure-sensitive adhesive layer out of the pressure-sensitive adhesive sheet with a protrudent push cutter blade, wherein, at at least an edge part of the protrudent push cutter blade, a cross-sectional shape of the protrudent push cutter blade, which is in a direction perpendicular to the direction in which the protrudent push cutter blade extends, has an angle a and an angle b, in which the angle a is larger than the angle b, wherein, in the cross-sectional shape, the angle a is an angle between a blade center line extending through a blade tip and a straight line corresponding to a side of the protrudent push cutter blade where the side faces the adhesive patch side, and the angle b is an angle between the blade center line extending through the blade tip and a straight line corresponding to another side of the protrudent push cutter blade where the side does not face the adhesive patch side, wherein angle a is 15 to 47.5° and angle b is 2.5 to 27.5°.

2. The process according to claim 1, wherein the protrudent push cutter blade cuts the pressure-sensitive adhesive sheet from the backing side to the release liner side.

3. The process according to claim 1, wherein the adhesive patch is punched out of the pressure-sensitive adhesive sheet with a die-cutting roll equipped with a die cutter having the protrudent push cutter blade and an anvil roll.

4. The process according to claim 1, wherein at least a part of the edge of the pressure-sensitive adhesive layer of the adhesive patch is located on the adhesive patch center side with respect to either the edge of the backing or the edge of the release liner.

5. The process according to claim 1, wherein the sum of the angle a and the angle b is 17.5 to 55 degrees.

6. The process according to claim 1, wherein the edge of the release liner of the adhesive patch is located on the adhesive patch periphery side with respect to a position on the release liner where a perpendicular segment drawn from the edge of the backing of the adhesive patch to the release liner intersects the release liner.

7. The process according to claim 1, wherein the pressure-sensitive adhesive layer contains an organic liquid ingredient.

8. The process according to claim 1, wherein the pressure-sensitive adhesive layer has a thickness of 100 μm or larger.

9. The process according to claim 1, wherein the pressure-sensitive adhesive layer contains a drug.

* * * * *